United States Patent [19]

Cregg et al.

[11] Patent Number: 4,818,700
[45] Date of Patent: Apr. 4, 1989

[54] PICHIA PASTORIS ARGININOSUCCINATE LYASE GENE AND USES THEREOF

[75] Inventors: James M. Cregg, San Diego, Calif.; George T. Sperl, Gurnee, Ill.

[73] Assignee: Phillips Petroleum Company, Bartlesville, Okla.

[21] Appl. No.: 791,485

[22] Filed: Oct. 25, 1985

[51] Int. Cl.[4] .................... C12N 1/20; C12N 9/88; C12N 1/16; C07H 15/12
[52] U.S. Cl. ...................... 435/252.33; 435/232; 435/849; 435/255; 435/938; 435/320; 435/91; 435/172.5; 536/27; 935/14; 935/28; 935/60; 935/64; 935/73
[58] Field of Search ............... 435/68, 69, 91, 70, 435/172.3, 255, 256, 320, 938, 172.1, 232, 849; 536/27; 935/14, 28, 56, 60, 64

[56] References Cited

U.S. PATENT DOCUMENTS 4,617,274 10/1926 Wegner ..................... 435/255

OTHER PUBLICATIONS

Kunze et al, *Curr. Genet*, vol. 9(3) Mar. 1985, pp. 205–209, "Transformation of *Candida Maltosa* and *Pichid guillermoandii* by a Plasmid Containing Saccharomyces".

Stinchomb et al., *Proc. Natl. Acad. Si.* vol. 77 (8) Aug. 1980, pp. 4559–4563, "Eukaryotic DNA Segments Capable of Autonomous Replication in Yeast".

Broach et al, *Gene*, vol. 8, 1979 pp. 121–133, "Transformation in Yeast: Development of a Hybrid Cloning Vector and Isolation of the Carl Gene".

Driscoll Renn et al, *Proc. Natl. Acad. Sci.*, vol. 80, pp. 270–278 May 1983 "Identiication of AAS Genes and Their Regulatory Role in General Control to Amino Acid Biosynthesion Yeast".

Messenguy et al, *Mol Gen Genet*, 1983, vol. 189, pp. 148–156, "Participation of Transcriptional and Post-Transcriptional Regulatory Mechanisms in the Control …".

*Gene*, vol. 29, I. R. Beacham et al, pp. 271–279 (1984).

*Primary Examiner*—Robin Teskin
*Attorney, Agent, or Firm*—J. E. Phillips

[57] ABSTRACT

Novel DNA sequences which code for the production of the Pichia protein argininosuccinate lyase are provided. Novel constructs including these sequences, as well as organisms transformed therewith are provided. In addition, novel strains of Pichia defective in argninosuccinate lyase activity are also provided.

5 Claims, 6 Drawing Sheets

PICHIA PASTORIS ARGININOSUCCINATE LYASE GENE AND USES THEREOF

This invention relates to the field of recombinant DNA technology. In one of its aspects, the invention relates to the isolation of functional genes from yeast strains of the genus Pichia. In another aspect, the invention relates to the use of such genes as selectable markers in transformation of yeast strains of the genus Pichia. In yet another aspect, the invention relates to novel yeast strains of the genus Pichia.

BACKGROUND

Up to now, commercial efforts employing recombinant DNA technology for producing various polypeptides have centered *Escherichia coli* as a host organism. However, in some situations *E. coli* may prove to be unsuitable as a host. For example, *E. coli* contains a number of toxic pyrogenic factors that must be eliminated from any polypeptide useful as a pharmaceutical product. The efficiency with which this purification can be achieved will, of course, vary with the particular polypeptide. In addition, the proteolytic activities of *E. coli* can seriously limit yields of some useful products. These and other considerations have led to increased interest in alternative hosts, in particular, the use of eukaryotic organisms for the production of polypeptide products is appealing.

The availability of means for the production of polypeptide products in eukaryotic systems, e.g., yeast, could provide significant advantages relative to the use of prokaryotic systems such as *E. coli* for the production of polypeptides encoded by recombinant DNA. Yeast has been employed in large scale fermentations for centuries, as compared to the relatively recent advent of large scale *E. coli* fermentations. Yeast can generally be grown to higher cell densities than bacteria and are readily adaptable to continuous fermentation processing. In fact, growth of yeast such as *Pichia pastoris* to ultra-high cell densities, i.e., cell densities in excess of 100 g/L, is disclosed by Wegner in U.S. Pat. No. 4,414,329 (assigned to Phillips Petroleum Co.). Additional advantages of yeast hosts include the fact that many critical functions of the organism, e.g., oxidative phosphorylation, are located within organelles, and hence not exposed to the possible deleterious effects of the organism's production of polypeptides foreign to the wild-type host cells. As a eukaryotic organism, yeast may provide capable of glycosylating expressed polypeptide products where such glycosylation is important to the bioactivity of the polypeptide product. It is also possible that as a eukaryotic organism, yeast will exhibit the same codon preferences as higher organisms, thus tending toward more efficient production of expression products from mammalian genes or from complementary DNA (cDNA) obtained by reverse transcription from, for example, mammalian mRNA.

The development of poorly characterized yeast species as host/vector systems is severely hampered by the lack of knowledge about transformation conditions and suitable vectors. In addition, auxotrophic mutations are often not available, precluding a direct selection for transformants by auxotrophic complementation. If recombinant DNA technology is to fully sustain its promise, new host/vector systems must be devised which facilitate the manipulation of DNA as well as optimize expression of inserted DNA sequences so that the desired polypeptide products can be prepared under controlled conditions and in high yield.

A basic element employed in recombinant DNA technology is the plasmid, which is extrachromosomal, double-stranded DNA found in some microorganisms. Where plasmids have been found to naturally occur in microorganisms, they are often found to occur in multiple copies per cell. In addition to naturally occurring plasmids, a variety of man-made plasmids, or hybrid vectors, have been prepared. Included in the information encoded in plasmid DNA is that required to reproduce the plasmid in daughter cells, i.e., an autonomous replication sequence. One of more phenotypic selection characteristics must also be included in the information encoded in the plasmid DNA. The phenotypic selection characteristics permit clones of the host cell containing the plasmid of interest to be recognized and selected by preferential growth of the cells in selective media.

OBJECTS OF THE INVENTION

An object of the invention, therefore, is functional genes from yeast strains of the genus Pichia, useful, for example, as phenotypic selection markers.

Another object of the invention is the isolation and characterization of the gene encoding argininosuccinate lyase (ARG4) from *Pichia pastoris*.

Yet another object of the invention is the transformation of yeast strains of the genus Pichia with transforming DNA including the ARG4 gene as a marker gene.

Still another object of the invention is novel strains of Pichia defective in argininosuccinate lyase (ARG4) activity.

These and other objects of the invention will become apparent from the disclosure and claims herein provided.

STATEMENT OF THE INVENTION

In accordance with the present invention, there has been discovered, isolated and characterized the gene encoding argininosuccinate lyase (The ARG4 gene) from a strain of yeast of the genus Pichia. The novel gene which has been isolated is useful as a phenotypic selection marker in a host/vector system employing yeast strains of the genus Pichia as host.

In accordance with another embodiment of the invention, there is provided a strain of Pichia defective in argininosuccinate lyase (ARG4) gene activity. This novel strain is useful as a host organism for transformation with transforming DNA which includes the ARG4 gene function as a phenotypic selection marker.

The following abbreviations are used throughout this specification to represent the restriction enzymes employed:

| Abbreviation | Restriction Enzyme |
|---|---|
| B | BamHI |

-continued

| Abbreviation | Restriction Enzyme |
| --- | --- |
| $B_2$ | BglII |
| $H_3$ | HindIII |
| $Hp_1$ | HpaI |
| Nr | NruI |
| Ps | PstI |
| $Pv_2$ | PvuII |
| $R_1$ | EcoRI |
| $R_5$ | EcoRV |
| S | SalI |
| Sp | SphI |
| $S_3$ | Sau3AI |
| Xh | XhoI |

In the attached figures, restriction sites employed for the manipulation of DNA fragments but which are destroyed upon ligation, are indicated by enclosing the abbreviation for the destroyed site in parenthesis.

DETAILED DESCRIPTION OF THE INVENTION

It has been discovered that the function genes from microorganisms of the genera Pichia and Saccharomyces are sufficiently similar to allow one to take advantage of well-characterized defective strains of Saccharomyces cerevisiae in order to isolate complementary functional genes from Pichia. Thus, in accordance with the present invention, a gene equivalent to the Saccharomyces ARG4 gene has been isolated from Pichia. This novel gene which has been isolated is referred to for purposes of this disclosure as the Pichia ARG4 gene. This novel gene has been isolated by transforming appropriate mutants of S. cerevisiae with a library of Pichia chromosomal DNA and selecting for transformed strains which survive in the absence of arginine supplementation in the media.

Isolation and Characterization of Pischi pastoris ARG4 Gene

Figure 1:
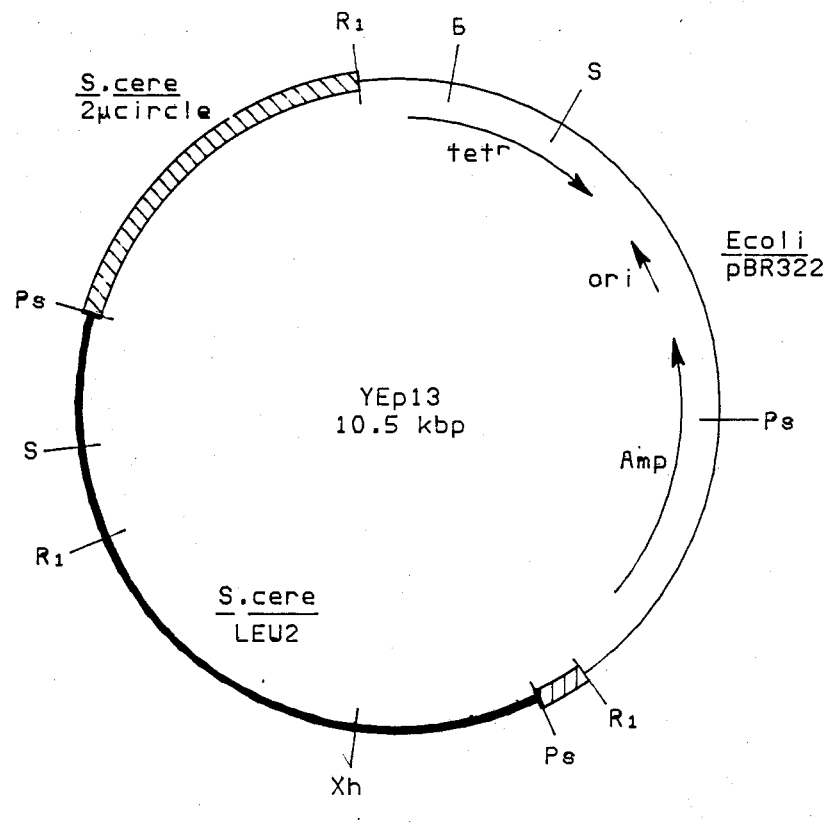
FIG. 1 is a restriction map of plasmid YEp13.

The ARG4 gene was isolated from the strain P. pastoris NRRL Y-11430 by partial digestion of total chromosomal DNA with Sau3AI followed by centrifugation through sucrose gradients. (See Example IV). Fragments of 5 to 20 kbp were cloned into the BamHI cleavage site of the S. cerevisiae-E. coli shuttle vector YEp13 (ATCC 37115; FIG. 1) and transformed into E. coli. Approximately 50,000 colonies were combined and total plasmid DNA extracted. Spheroplasts of S. cerevisiae strain S2072A (a arg4 leu1 trp1 gal2; available from the Yeast Genetic Stock Center, Berkeley, Calif.), an arg4 mutant, were mixed with about 1 μg of the YEp13 Pichia DNA library by the procedure of Hinnen et al. (1978) and allowed to regenerate in a medium deficient in arginine. The transformation resulted in 45 prototrophic yeast colonies from a population of $1 \times 10^7$ total regenerable spheroplasts. A parallel control sample incubated without DNA produced one colony.

Plasmids were recovered from seven of the Arg+ S. cerevisiae colonies by extracting total DNA from yeast cells and transforming the DNA into E. coli. Each of the seven plasmids appeared to contain the ARG4 gene, since each was able to transform the S. cerevisiae arg4 strain S2072A to arginine prototrophy at high frequency. The plasmids were characterized by restriction enzyme mapping. Six of the plasmids were composed of YEp13 plus an identical 8.2 kbp insert of Pichi DNA. One plasmid was composed of YEp13 plus an insert of about 10 kbp which included most or all of the sequences found in the six smaller plasmids.

Figure 2:
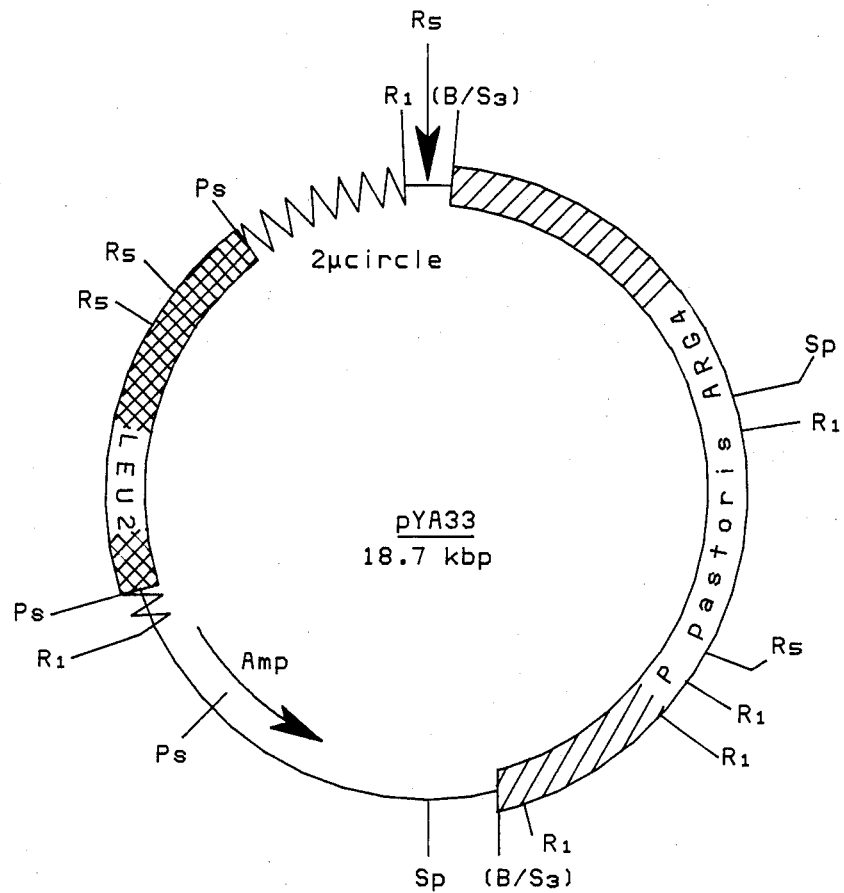
FIG. 2 is a restriction map of plasmid pYA33.
Figure 3:
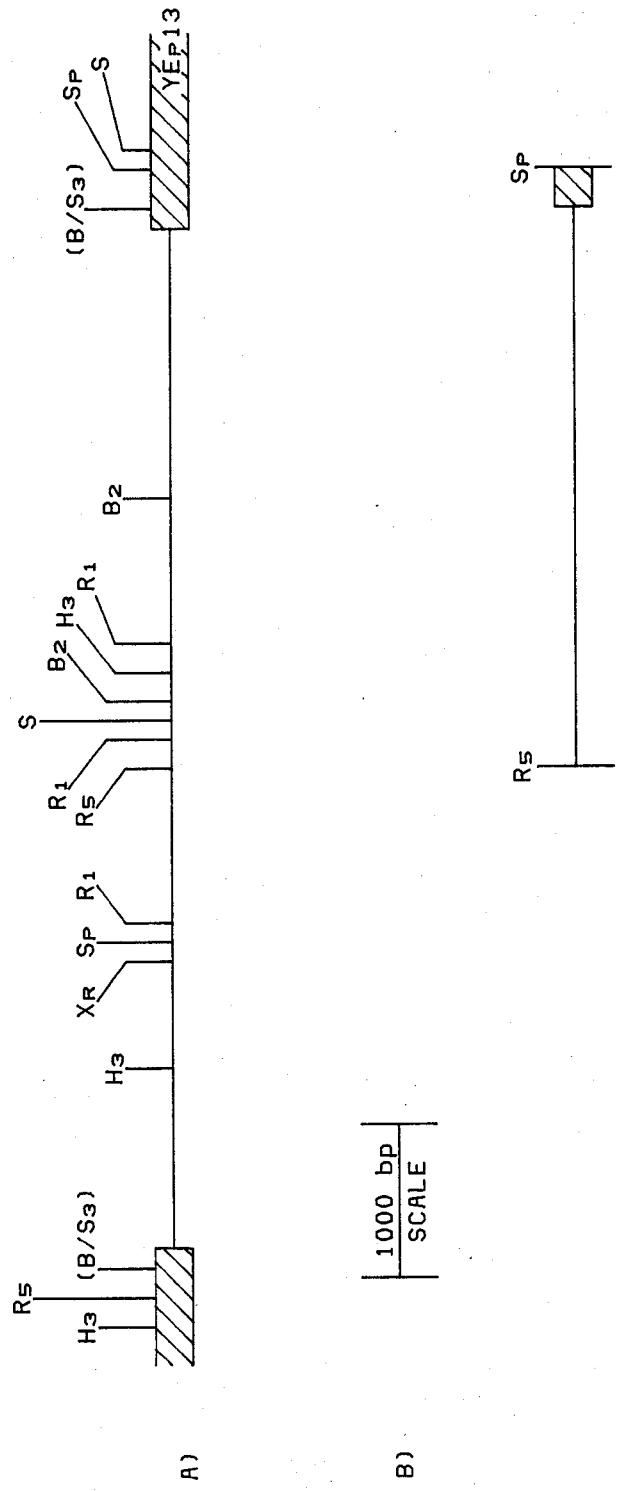
FIG. 3 is a restriction map of an 8.2 kilobase pair (kbp) fragment of Pichia chromosomal DNA which contains the Pichia ARG4 gene. Also shown is a specific subfragment of the gene.

One of the smaller plasmids, pYA33, (FIG. 2) was selected for further analysis. This plasmid, carried in the E. coli host MC1061, has been deposited with the Northern Regional Research Center of the U.S. Department of Agriculture in Peoria, Ill. to insure access to the public upon issuance of this application as a patent. Strain MC1061-pYA33 has been assigned the accession number NRRL B-18016. A detailed restriction map of the DNA fragment from pYA33 which contains the ARG4 gene is presented in FIG. 3a. Referring to the 5' (left) BamHI/Sau3AI junction of the 8.2 kbp DNA fragment as the origin, the following cleavage pattern is obtained:

| Restriction Enzyme | Cleavage Sites | Distance from Origin (bp) |
| --- | --- | --- |
| $R_1$ | 3 | 4,000; 5,500; 6,000 |
| $H_3$ | 2 | 3,000; 6,000 |
| $B_2$ | 2 | 5,900; 6,700 |
| S | 1 | 5,800 |
| Sp | 1 | 3,900 |
| Xh | 1 | 3,700 |

Southern blot analysis in which restriction fragments from pYA33 were cross-hybridized with a labelled fragment containing the S. cerevisiae ARG4 gene at low stringency (post hybridization washes in 2x SSC at 55° C.; SSC is 0.15 M NaCl and 15 mM sodium citrate adjusted to pH 7.0 with NaOH) showed that plasmid pYA33 contains sequences homologous to the S. cerevisiae ARG4 gene and that these sequences are located in the 3'-most portion of the 8.2 kbp Pichia DNA insert of pYA33.

Figure 5:
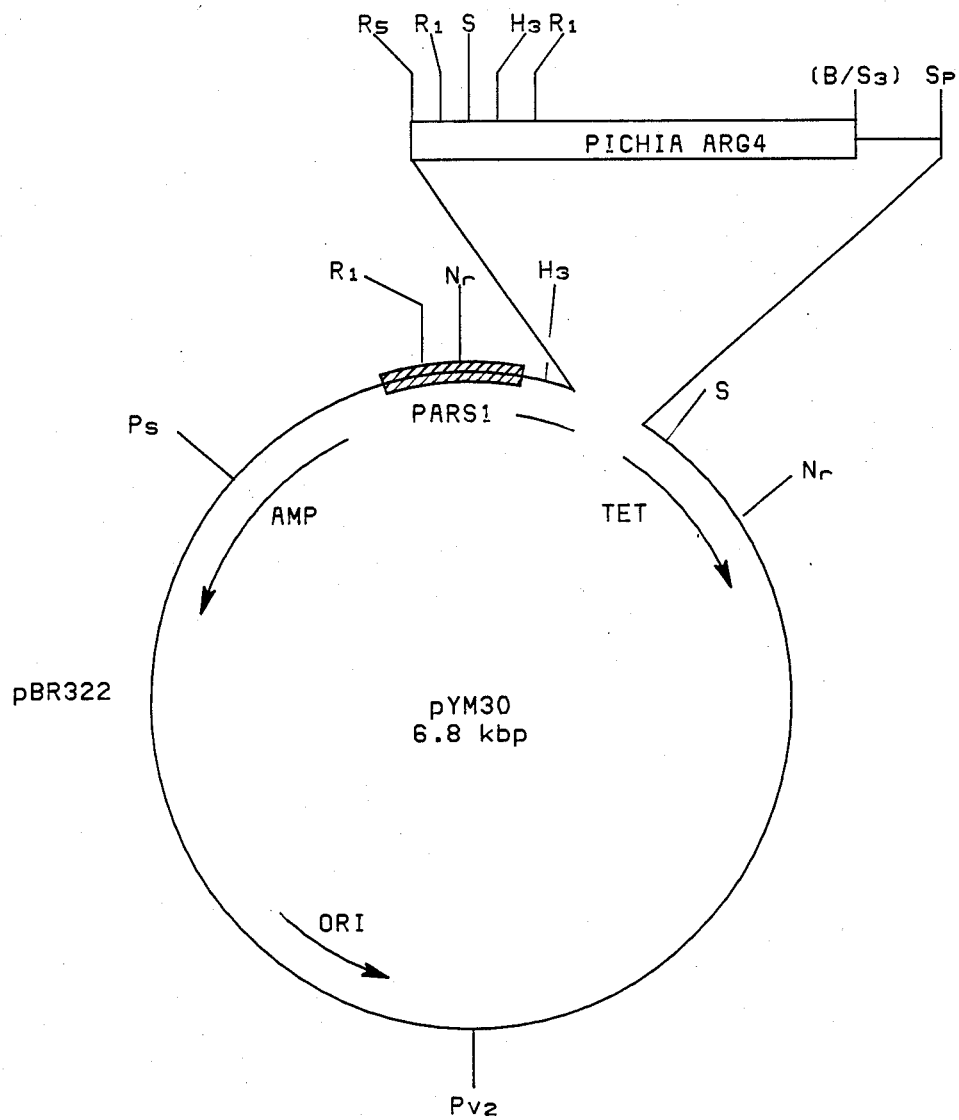
FIG. 5 is a restriction map of plasmid pYM30.

By subcloning of this 8.2 kbp fragment, it was determined that a 2.7 kbp EcoRV-SphI fragment of this Pichia DNA retained the ability to transform Pichia or Saccharomyces strains defective in argininosuccinate lyase. Thus, for example, Pischi pastoris NRRL Y-18014 (GS190), an arg4 mutant, is able to grow on media without arginine supplementation when transformed with plasmid pYM30, shown in FIG. 5. Plasmid pYM30 contains the 2.7 kbp EcoRV-SphI fragment of DNA shown in FIG. 3b of the drawings.

In accordance with another embodiment of the present invention, the auxotrophic mutant GS190 (NRRL Y-18014) was isolated and determined to be defective in the arginine pathway, in that the strain has no argininosuccinate lyase activity. See the assay procedure in Example II for more detail.

Those of skill in the art recognize that mutation frequencies can be increased in a variety of ways, such as, for example, by subjecting exponentially growing cells to the action of a variety of mutagenic agents, such as, for example, N-methyl-N'-nitro-N-nitrosoguanidine, ethyl methanesulfonate, ultraviolet irradiation and the like. Isolation and identification of mutant strains defective in a specific metabolic pathway can be accomplished by determining the nutrient or nutrients required by the strain for growth as detailed, for example, in Example I. The specific gene and gene product in which a mutant strain is defective can then be determined by identifying the enzymatic activity which is absent, as detailed, for example, in Example II.

The auxotrophic mutant GS190 (NRRL Y-18014) and the ARG4 gene from Pichia, each provided in accordance with the present invention, together provide a transformation system useful for introducing heterologous DNA into Pichia. The ARG4 gene provides the gene encoded activity in which the auxotrophic mutant host is defective, thereby facilitating selection of those hosts which have incorporated transforming DNA.

The invention will now be described in greater detail by reference to the following non-limiting examples.

EXAMPLES

The buffers and solutions employed in the following examples have the compositions given below:

| | |
|---|---|
| 1M Tris buffer | 121.1 g Tris base in 800 mL of $H_2O$; adjust pH to the desired value by adding concentrated (35%) aqueous HCl; allow solution to cool to room temperature before final pH adjustment; dilute to a final volume of 1 L. |
| TE buffer | 1.0 mM EDTA in 0.01 M (pH 7.4) Tris buffer |
| LB (Luria-Bertani) Medium | 5 g Bacto-tryptone<br>5 g Bacto-yeast extract<br>2.5 g NaCl<br>in 1 L of water, adjusted to pH 7.5 with NaOH |
| 2B Medium | 0.2% $NH_4PO_4$<br>1.2% $Na_2HPO_4$<br>0.013% $MgSO_4.7H_2O$<br>0.074% $CaCl_2.2H_2O$<br>1 µg/mL thiamine<br>0.4% dextrose |
| YPD Medium | 1% Bacto-yeast extract<br>2% Bacto-peptone<br>2% Dextrose |
| SD Medium | 6.75 g yeast nitrogen base without amino acids (DIFCO)<br>2% Dextrose in 1 L of water |
| SED | 1 M Sorbitol<br>25 mM EDTA<br>50 mM DTT |
| SCE Buffer | 9.1 g Sorbitol<br>1.47 g Sodium citrate<br>0.168 g EDTA<br>50 mL $H_2O$<br>pH to 5.8 with HCl |
| CaS | 1 M Sorbitol<br>10 mM $CaCl_2$<br>filter sterilize |
| PEG Solution | 20% polyethylene glycol-3350<br>10 mM $CaCl_2$<br>10 mM Tris-HCl (pH 7.4)<br>filter sterilize |
| SOS | 1 M Sorbitol<br>0.3x YPD medium<br>10 mM $CaCl_2$ |
| MM (minimal) medium) | 0.875 g $KH_2PO_4$<br>0.125 g $K_2HOP_4$<br>1.0 g $(NH_4)_2SO_4$<br>0.5 g $MgSO_4.7H_2O$<br>0.1 g NaCl<br>0.05 mg $FeCl_3.6H_2O$<br>0.07 mg $ZnSO_4.7H_2O$<br>0.01 mg $H_3BO_3$<br>0.01 mg $CuSO_4.5H_2O$<br>0.01 mg KI<br>0.1 g $CaCl_2.2H_2O$<br>per liter of sterile $H_2O$ |
| MM "minus" | MM formulation without $(NH_4)_2SO_4$ |
| Citrate buffer | 9.79 g sodium citrate<br>3.2 g citric acid<br>dilute to 500 mL with $H_2O$<br>adjust to pH 5.5 with 1 N NaOH |
| Nystatin solution | 4.4 mg nystatin (5680 Units/mg)<br>1 mL dimethyl formamide<br>dilute to 10 mL with water |
| argininosuccinate solution | 50 mg barium argininosuccinate<br>9.85 mL $H_2O$<br>0.15 mL of 0.1 M $K_2SO_4$ |
| BUN Reagent | centrifuge to clarify and save supernatant<br>3 parts BUN acid reagent and 2 parts BUN color reagent; available from Sigma as diagnostic kit #535 |
| Vitamin Mix | p-aminobenzoic acid 50 mg/100 mL<br>p-hydroxybenzoic acid 50<br>riboflavin 25<br>pantothenate 50<br>$B_{12}$ 1<br>folic acid 50<br>pyridoxine 50<br>biotin 5<br>thiamine 10<br>nicotinic acid 50<br>inositol 2000 |

The following abbreviations are used throughout the examples with the following meaning:

| | |
|---|---|
| EDTA | ethylenediamine tetraacetic acid |
| SDS | sodium dodecyl sulfate |
| DTT | dithiothreitol |
| NTG | N—methyl-N'—nitro-N—nitrosoguanidine |
| BUN | Blood urea nitrogen |
| ala | alanine |
| arg | arginine |
| asn | asparagine |
| asp | aspartic acid |
| cys | cysteine |
| glu | glutamic acid |
| gln | glutamine |
| gly | glycine |
| his | histidine |
| ile | isoleucine |
| leu | leucine |
| lys | lysine |
| met | methionine |
| phe | phenylalanine |
| pro | proline |
| ser | serine |
| thr | threonine |
| trp | tryptophan |
| tyr | tyrosine |
| val | valine |

EXAMPLE I

Isolation of Auxotrophic Mutants

A. Pichia Mutagenesis

A culture of a selected yeast strain, such as for example, *Pischi pastoris* NRRL Y-11430, was inoculated into 100 mL of YPD broth and incubated at 30° C. on a shaker for about 12-20 hrs. About 40 mL of the resulting culture were spun down at about 2,000 g for 5 minutes. The cells were then washed twice with 40 mL aliquots of sterile 0.1 M citrate buffer (pH 5.5). Washed cells were resuspended in 36 mL of sterile citrate buffer, then treated with 4 mL of NTG solution containing 5 mg of NTG per mL—thus giving a final NTG concentration of 500 µg/mL. Cells in the presence of NTG were allowed to stand for about 30 minutes at room temperature without agitation.

NTG was then removed by washing the cells twice with 40 mL aliquots of sterile deionized water. Sufficient YPD medium was used to resuspend washed cells, which were then transferred to a flask and total volume brought up to 100 mL with additional YPD. These mutagenized cells were then incubated at 30° C. on a shaker for about 48 hours.

After incubation, about 40 mL of the yeast containing solution were spun down at 2,000 g for 5 minutes. The cell pellet was washed twice with 40 mL aliquots of sterile, deionized water, then suspended in 40 mL of MM "minus" media plus 1% glucose carbon source and 5 μg/mL biotin and incubated at 30° C. on a shaker for 12-20 hours.

B. Nystatin Enrichment

Five mL of the above culture grown on glucose was used to inoculate 100 mL of "restricted media". Restricted media comprises the MM formulation plus carbon source (typically 1% glucose), vitamin/amino acid supplementation as appropriate (such as the "vitamin mix" referred to above), except no supplementation is provided for the metabolite produced by the biosynthetic pathway in which a defect is sought. For example, where a leucine auxotroph is desired, no leucine supplementation will be provided. The inoculum in restricted media was incubated at 30° C. in a shake flask and monitored periodically on a Klett-Summerson photoelectric colorimeter equipped with a 500-570 millimicron green filter. Incubation was contained until the scale reading (which is proportional to optical density) has increased 20-305 with respect to the original scale reading.

When the scale reading had increased as desired, the solution was treated with 1 mL of Nystatin solution, giving a Nystatin content of about 25 units/mL in the solution. The Nystatin-treated solution was incubated at 30° C. for 90 minutes without agitation, at which time 40 mL of the solution was spun down and the cells washed twice with 40 mL aliquots of deionized water. Washed cells were then diluted as appropriate in order to obtain about 100-150 colonies per plate. Colonies were plated on mutant growth media which consists of MM media, carbon source (typically 1% glucose), 5μg biotin and supplementation for any metabolite produced by the biosynthetic pathway in which the mutational defect is sought.

The colonies plated on mutant growth media were replica plated onto media formulation absent the metabolite supplementation. The original and replica plates were incubated at 30° for at least 48 hours. Those colonies that grew on the original plate (on mutant growth media) but not on the replica plates were selected for further characterization.

The auxotrophic mutants selected were transferred to metabolic pool plates and incubated at 30° C. for at least 48 hours in order to determine in which pathway(s) mutational defects existed.

Pool plates were prepared by dissolving 10mg/mL of the L-isomer of each of 5 different amino acids, as follows:

| | 1 | 2 | 3 | 4 | 5 |
|---|---|---|---|---|---|
| 6 | gly | asn | cys | met | gln |
| 7 | his | leu | ile | val | lys |
| 8 | phe | tyr | trp | thr | pro |
| 9 | glu | ser | ala | asp | arg |

Thus, plate 1 contains 10 mg/mL each of glycine, histidine phenylalanine and glutamic acid; plate 2 contains 10 mg/mL each of asparagine, lecuine, tyrosine, and serine, and so on. A tenth plate was prepared by dissolving a 1 g of Casamino acids in 1 L of sterile water.

An aliquot of 250 μL of each of amino acid pools 1-10 was applied to plates containing minimal media plus 1% glucose, and the plates allowed by dry overnight.

The mutational defect of a given mutant can be determined by inspection of the growth pattern on the various pool plates. Thus, GS190, a mutant defective in the arginine pathway, grew only on pool plates 5, 9 and 10, but did not grow on the other pool pates which did not have arginine supplementation.

EXAMPLE II

Identification of *Pischi pastoris* Mutants Defective in Argininosuccinate Lyase Activity

A. Plate Test

Initial screening of arginine requiring mutants prepared as described in Example I was carried out to identify mutants defective at the arg4 locus (i.e., lacking argininosuccinate lyase activity). A master plate of arginine auxotrophic mutants was prepared with MM media, 1% glucose, vitamin mix (1 mL per L of media) and 0.2% Casamino acids. The master plate was incubated at 30° C. for at least 48 hours, then five replica plates were prepared from the master plate:

(1) MM media+1% glucose+vitamin mix+0.02% citrulline;

(2) MM media+1% glucose+vitamin mix+0.02% ornithine;

(3) MM media+1% glucose+vitamin mix+0.02% arginine;

(4) MM media+1% glucose+vitamin mix;

(5) MM media+1% glucose+vitamin mix+0.2% casamino acids.

These 5 plates were incubated at 30° C. for at least 48 hours. Those colonies which grew on plates (3) and (5), but did not grow on plates (1), (2) or (4) were selected for further analysis.

B. Enzymatic Analysis

The first step in the argininosuccinate lyase assay procedure was to grow a 100 mL culture of a strain in YPD medium with shaking at 30° C. to an $OD_{600}$ of 1.0. The culture was then centrifuged at about 12,000 g for 5 minutes, washed one time with sterile deionized water, and the cells were resuspended in 5 mL of minimal media (MM)+1% glucose+0.1% vitamin mix and incubated with shaking at 30° C. for 12-15 hours.

The next step was to prepare a cell extract from the culture. Cells were harvested by centrifugation at about 12,000 g for 5 min., washed once with 0.2 M potassium phosphate buffer (pH 9.0), then resuspended in 5 mL of 0.2 M potassium phosphate buffer (pH 9.0). The cells were ruptured by passing the sample through an Aminco French pressure cell which had a one inch diameter piston using an Aminco French press at a cell pressure of about 16,000 PSI. The pressure cell was held on ice until use, the procedure was performed at about 4° C., and the samples were kept on ice after cell breakage. To monitor cell breakage, a 10 μL sample was added to 10 mL of $H_2O$ and its $OD_{600}$ determined and compared to an identically prepared control sample which had not been passed through the pressure cell. If the optical density of the treated sample was greater than 50% of the control, the sample was subjected to the disruption procedure a second time. The extract was then centrifuged at about 12,000 g and 4° C. for 10 minutes to remove cell debris. The supernatant was removed and stored on ice pending assay for enzyme activity.

The argininosuccinate lyase activity of the cell extracts was determined by measuring the rate of argininosuccinate conversion to urea in a coupled assay system containing arginase. The formation of urea was determined employing a BUN reagent kit. For each extract to be assayed, a reaction mixture as follows was prepared:

---
0.1 mL arginase (1 unit)
0.1 mL of 0.1 M MnCl$_2$
mix for 5 minutes, then add
0.1 mL argininosuccinate solution
0.25 mL of 0.2 M potassium phosphate buffer (pH 9.0)
0.1 mL cell extract
bring volume to 1 mL with deionized water
---

A 20–100 μL sample of the reaction mixture prepared as described in the previous paragraph was added to 5 mL of BUN Reagent in a 13×100 mm glass tube. The tubes were placed in a boiling water bath for exactly 10 minutes, then removed from the boiling water bath and immediately placed on ice for 3–5 minutes.

The optical density of each reaction tube was determined by taking a Klett reading with a green filter at times of 0.0, 0.33, 1.0 and 13.0 hours. As a control, extracts prepared from *Pischi pastoris* NRRL Y-11430 were assayed in parallel.

*Pischi pastoris* NRRL Y-11430, a wild type strain requiring no amino acid supplementation, gave an OD$_{340}$ of about 0, 6, 14 and 378 at 0, 0.33, 1.0 and 13.0 hours, respectively. In contrast, one such *Pischi pastoris* mutant, designated GS190 and deposited with the Northern Regional Research Center having the accession number NRRL Y-18014, gave an OD$_{340}$ of essentially zero at all time points. Consistent with the mutant genotype nomenclature employed for *S. cerevisiae*, GS190 has been designated as an arg4 mutant strain.

EXAMPLE III

*Pischi pastoris* Transformation Procedure

A. Cell Growth

1. Inoculate a colony of *Pischi pastoris* GS190 (NRRL Y-18014) into about 10 mL of YPD medium and shake culture at 30° C. for 12–20 hrs.
2. After about 12–20 hrs., dilute cells to an OD$_{600}$ of about 0.01–0.1 and maintain cells in log growth phase in YPD medium at 30° C. for about 6–8 hrs.
3. After about 6–8 hrs, inoculate 100 mL of YPD medium with 0.5 mL of the seed culture at an OD$_{600}$ of about 0.1 (or equivalent amount). Shake at 30° C. for abour 12–20 hrs.
4. Harvest culture when OD$_{600}$ is about 0.2–0.3 (after approximately 16–20 hrs) by centrifugation at 1500 g for 5 minutes.

B. Preparation of Spheroplasts

1. Wash cells once in 10 mL of sterile water. (All centrifugations for steps 1–5 are at 1500 g for 5 minutes.)
2. Wash cells once in 10 mL of freshly prepared SED.
3. Wash cells twice in 10 mL of sterile 1 M Sorbitol.
4. Resuspend cells in 10 mL SCE buffer.
5. Add 5–10 μL of 4 mg/mL Zymolyase 60,000 (Miles Laboratories). Incubate cells at 30° C. for about 30–60 minutes.

Since the preparation of spheroplasts is a critical step in the transformation procedure, one should monitor spheroplast formation as follows: add 100 μL aliquots of cells to 900 μL of 5% SDS and 900 μL of 1 M Sorbitol before or just after the addition of zymolyase and at various times during the incubation period. Stop the incubation at the point where cells lyse in SDS but not in sorbitol (usually between 30 and 60 minutes of incubation).

6. Wash spheroplasts twice in 10 mL of sterile 1 M Sorbitol by centrifugation at 1000 g for 5–10 minutes. (The time and speed for centrifugation may vary; centrifuge enough to pellet spheroplasts but not so much that they rupture from the force.)
7. Wash cells once in 10 mL of sterile CaS.
8. Resuspend cells in total of 0.6 mL of CaS.

C. Transformation

1. Add DNA samples (up to 20 μL volume) to 12×75 mm sterile polypropylene tubes. (DNA should be in water or TE buffer; for maximum transformation frequencies with small amounts of DNA, it is advisable to add about 1 μL of 5 mg/mL sonicated *E. coli* DNA to each sample.)
2. Add 100 μL of spheroplasts to each DNA sample and incubate at room temperature for about 20 minutes.
3. Add 1 mL of PEG solution to each sample and incubate at room temperature for about 15 minutes.
4. Centrifuge samples at 1000 g for 5–10 minutes and decant PEG solution.
5. Resuspend samples in 150 μL of SOS and incubate for 30 minutes at room temperature.
6. Add 850 μL of sterile 1 M Sorbitol and plate aliquots of samples as described below.

D. Regeneration of Spheroplasts

1. Recipe for Regeneration Agar Medium a. Agar-KCl - 9 g Bacto-agar, 13.4 g KCl, 240 mL H$_2$O, autoclave.
b. 10X Glucose- 20 g Dextrose, 100 mL H$_2$O, autoclave
c. 10X SC- 6.75 g Yeast Nitrogen Base without amino acids, 100 mL H$_2$O, autoclave. (Add any desired amino acid or nucleic acid up to a concentration of 200 μg/mL before or after autoclaving.)
d. Add 30 mL of 10X Glucose and 30 mL of 10X SC to 300 mL of the melted Agar-KCl solution. Add 0.6 mL of 0.2 mg/mL biotin and any other desired amino acid or nucleic acid to a concentration of 20 μg/mL. Hold melted Regeneration Agar at 55°–60° C.

2. Plating of Transformation Samples

Pour bottom agar layer of 10 mL Regeneration Agar per plate at least 30 minutes before transformation samples are ready. Distribute 10 mL aliquots of Regeneration Agar to tubes in a 45°–50° C. bath during the period that transformation samples are in SOS. Add aliquots of transformation samples described above to tuber with Regeneration Agar and pour onto bottom agar layer of plates. Add a quantity of each sample to 10 mL aliquots of melted Regeneration Agar held at 45°–50° C. and pour each onto plates containing a solid 10 mL bottom agar layer of Regenation Agar.

3. Determination of Quality of Spheroplast Preparation

Remove 10 μL of one sample and dilute 100 times by addition to 990 μL of 1 M Sorbitol. Remove 10 μL of the 100 fold dilution and dilute an additional 100 times by addition to a second 990 μL aliquot of 1 M Sorbitol. Spread plate 100 μL of both dilutions on YPD agar medium to determine the concentration of unspheroplasted whole cells remaining in the preparation. Add 100 μL of each dilution to 10 mL of Regeneration Agar supplemented with 50 μg/mL arginine to determine total regeneratable spheroplasts. Good values for a transformation experiment are $1-3 \times 10^7$ total regeneratable spheroplasts/mL and about $1 \times 10^3$ whole cells/mL.

4. Incubate plates at 30° C. for 3-5 days.

EXAMPLE IV

Isolation of Pischi pastoris ARG4 Gene

A. Strains

The strains employed include:
(a) *Pischi pastoris* strain NRRL Y-11430;
(b) *Pischi pastoris* strain NRRL Y-18014 (GS190-arg4);
(c) *S. cerevisiae* strain S2072A (a arg4 leu1 trp1 gal2; available from the Yeast Genetic Stock Center, Berkely, Calif.); and
(d) *E. coli* strain 848 (F− met thi gal $T_1{}^R\phi 80^S$hsdR− hsdM+).

Figure 6:
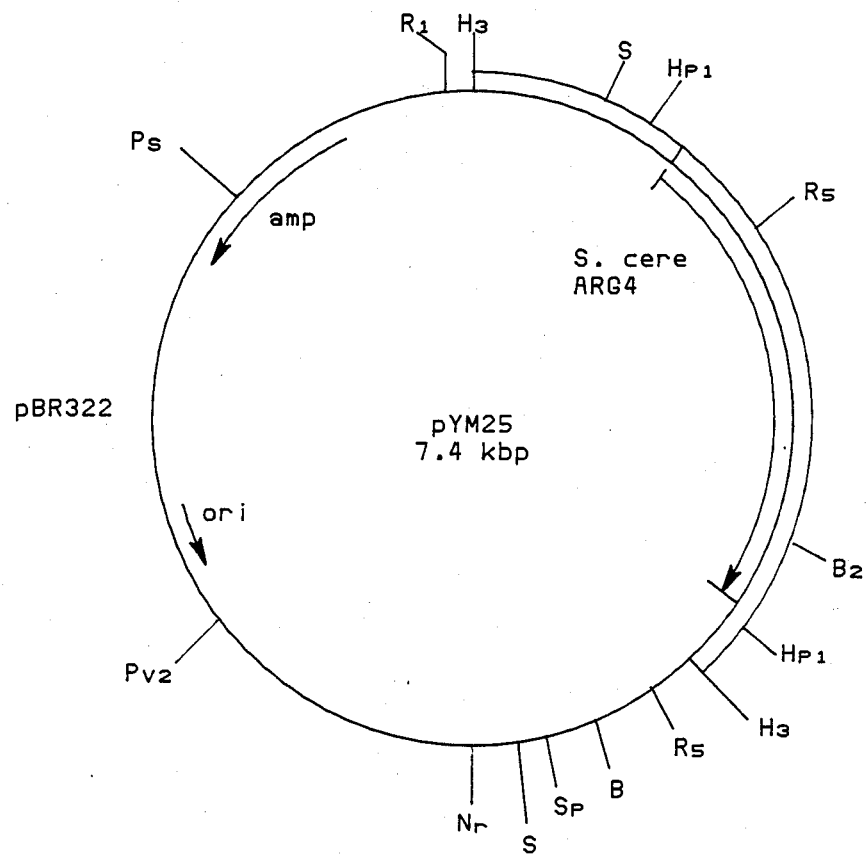
FIG. 6 is a restriction map of plasmid pYM25.

B. Plasmids pYM25 (see FIG. 6), which plasmid is a derivative of pGT27 (described by Tschumper and Carbon), consists of the *S. cerevisiae* ARG4 gene on a 3.1 kbp HindIII fragment inserted at the HindIII site of pBR322, was the source of the *S. cerevisiae* ARG4 gene fragments. Plasmid pYM25, carried in the *E. coli* host MC1061, has been deposited with the Northern Regional Research Center of the U.S. Department of Agriculture in Peoria, Illinois, and is available to the public as NRRL B-18015.

YEp13 is available from the American Type Culture Collection and has been assigned accession number ATCC 37115.

C. Media

*Pischi pastoris* was grown in YPD (rich) or Sd (minimal) media.

*E. coli* was cultured in either LB medium or 2B medium supplemented with 100 μg/mL tryptophan, and 0.2% Casamino acids.

D. DNA Isolation

1. Large Scale Preparations of Yeast DNA

Both *Pischi pastoris* and *S. cerevisiae* DNA preparations were carried out by grouping yeast cells in 100 mL of minimal medium until $A_{600}$ equals 1-2 and then harvesting the cells by centrifugation at 2,000 g for 5 minutes. The cells were washed once in H$_2$O, once in SED, once in 1 M sorbitol and then suspended in 5 mL of 0.1 M Tris-HCl (pH 7.0) which is 1 M in sorbitol. The cells were mixed with 50-100 μL of a 4 mg/mL solution of Zymolyase 60,000 (Miles Laboratories) and incubated at 30° C. for 1 hour to digest the cell walls. The spheroplast preparation was then centrifuged at 1000 g for 5-10 minutes and suspended in Lysis buffer (0.1% SDS, 10 mM Tris-HCl, (pH 7.4), 5 mM EDTA and 50 mM NaCl). Proteinase K (Boehringer Mannheim) and RNase A (Sigma) were each added to 100 μg/mL and the mixture incubated at 37° C. for 30 minutes. DNA was deproteinized by gently mixing the preparation with an equal volume of chloroform containing isoamyl alcohol (24:1, v/v) and the phases were separated by centrifugation at 12,000 g for 20 minutes. The upper (aqueous) phase was drawn off into a fresh tube and extracted with an equal volume of phenol/chloroform/isoamyl alcohol (25:24:1, v/v/v). The phases were separated as before and the top phase placed in a tube containing 2-3 volumes of cold 100% ethanol. The sample was gently mixed and DNA was collected by spooling onto a plastic rod. The DNA was immediately dissolved in 1 mL of TE buffer and dialyzed overnight at 4° C. against 100 volumes TE buffer.

2. Small Scale Yeast DNA Preparations

Five mL of yeast cultures in minimal medium were grown until $A_{600}$ equals 1-5 and harvested by centrifugation at 2,000 g for 5 minutes. Cells were suspended in 1 mL of SED and transferred to a 1.5 mL microfuge tube, washed once in 1 M sorbitol and resuspended in 0.5 mL of 0.1 M Tris-HCl (pH 7.4) which is 1 M sorbitol. Zymolyase 60,000 (Miles Laboratories; 10 μL of a 4 mg/mL solution) was added to each sample and the cells were incubated for 30-60 minutes at 30° C. Cells were then centrifuged for 1 minute, suspended in the Lysis buffer and incubated at 65°-70° C. After 15 minutes the samples were mixed with 100 μL of 5 M potassium acetate, held in an ice bath for 15 minutes and centrifuged for 5 minutes. The supernatants were decanted into a fresh microfuge tube containing 1 mL of 100% ethanol, mixed and immediately centrifuged for 10 seconds. Finally, the DNA pellets were air dried for 10-15 minutes and dissolved in 50 μL of TE buffer.

3. Large Scale *E. coli* DNA Preparations

*E. coli* cultures for large scale (0.5-1 L) plasmid preparations were grown at 37° C. with shaking in 2 B medium supplemented as described above and with the appropriate antibiotic. For cells which contained pBR322 derived plasmids, cultures were grown to an $A_{550}$ of about 0.7 at which time sufficient chloramphenicol was added to give a concentration of 100 μg/mL and cells harvested approximately 15 hours later. Strains which contained pBR325 derived plasmids were inoculated into the supplemented 2B medium at a starting $A_{550}$ of about 0.01-0.05 and incubated with shaking at 37° C. for 20-24 hours before harvesting. Plasmids were isolated by the alkaline lysis method described by Birnboim and Doly (1979).

4. Small Scale *E. coli* DNA Preparations

For small scale rapid plasmid isolations, 2 mL cultures in the supplemented 2B medium with antibiotic were grown overnight at 37° C. with shaking and harvested by centrifugation in 1.5 mL microfuge tubes. Plasmids were isolated by the alkaline lysis method described by Birnboim and Doly (1979).

E. Restriction of DNA and Fragment Isolation

Restriction enzymes were obtained from New England Biolabs and Bethesda Research Laboratories and digestions were performed by routine techniques. Restriction mappings were carried out by comparing parallel digestions of plasmids with and without insert DNA. Restriction fragments were purified by electroelution from agarose gels into Whatman 3 MM paper strips backed by dialysis tubing. The fragments were recovered from the paper and tubing by 3-4 washings with 0.1-0.2 mL volumes of a solution which contained 0.1 M NaCl, 50 mM Tris-HCl (pH 8.0) and 1 mM EDTA. Finally, the fragments were extracted with phenol/chloroform/isoamyl alcohol, precipitated with ethanol and redissolved in a small volume of TE buffer.

F. Construction of *Pischi pastoris* Library in *E. Coli*

For the *Pischi pastoris* DNA-YEp13 library construction, 100 μg of YEp13 was digested to completion with BamHI and treated with calf intestinal alkaline phosphatase to remove the terminal 5' phosphate from the DNA. A 100 μg aliquot of wild type *Pischi pastoris* DNA from *Pischi pastoris* NRRL Y-11430) was partially digested with 10 units of Sau3AI by incubation for 5 minutes at 37° C. in a total volume of 1 mL. Fragments of 5 to 20 kbp were size selected by centrifugation through 5–20% sucrose gradients. One μg of the vector and 2 μg of the Pichia Sau3AI fragments were mixed with 20 units of T4 DNA ligase (Bethesda Research Laboratories) in a total volume of 200 μL and incubated overnight at 4° C. The ligated DNAs were transformed into *E. coli* by adding the entire ligation reaction mix to 2 mL of competent *E. coli* 838 cells and incubating for 15 minutes at 0° C. The mixture was warmed to 37° C. for 5 minutes after which time 40 mL of LB medium was added and the 37° C. incubation continued for an additional 1 hour. Ampicillin was then added to give a total concentration of 100 μg/mL and the incubation continued for a second hour. Finally, the cells were centrifuged for 10 minutes at 3,000 g, resuspended in 1 mL of fresh LB medium and spread in equal aliquots on 10 LB agar plates containing 100 μg/mL of ampicillin. The approximately 50,000 colonies which resulted were scraped from the plates and a portion of the cells was inoculated into 500 mL of the supplemented 2B medium at a starting $A_{550}$ of about 0.1. The culture was grown and plasmid was extracted as described above. Of the colonies which were pooled for the library, 96 out of 100 tested were tetracycline sensitive and 7 out of 10 examined contained plasmids with insert DNA.

G. Souther Hybridizations

Hybridizations were carried out by the method of Southern (1975). For transfer of large or supercoiled DNA molecules to nitrocellulose, DNA was first partially hydrolyzed by soaking agarose gels in 0.25 M MCl for 10 minutes prior to alkali denaturation. All hybridizations of labelled fragments were performed in the presence of 50% formamide, 6x SSC, 5x Denhardt's, 0.1% SDS, 1 mM EDTA, and 100 μg/mL denatured herring sperm DNA at 42° C. Post-hybridization washes for hybridization of labelled fragments from the *S. cerevisiae* ARG4 gene to *Pischi pastoris* DNA were carried out under the low stringency conditions of 2x SSC, 1 mM EDTA, 0.1% SDS and 0.1% sodium pyrophosphate at 55° C.

H. $^{32}$P-Labelling

Nick translations were carried out accoridng to the procedure of Rigby et al. (1977).

I. Yeast Transformations

*S. cerevisiae* transformations were carried out by the spheroplast generation method of Hinnen et al. (1978).
*Pischi pastoris* transformations were performed following the procedure described above.

J. Isolation of Pichia ARG4 Gene

DNA fragments which contained the Pichia ARG4 gene were isolated from a Pichia DNA library by their ability to complement an *S. cerevisiae* arg4 strain. The library was composed of 5–20 kpb Sau3AI partial digestion fragments of wild type Pichia (NRRL Y-11430) DNA inserted into the BamHI site of the *S. cerevisiae-E. coli* shuttle vector YEp13. Spheroplasts of *S. cerevisiae* S2072A (an arg4 strain) were generated by the technique of Hinnen et al. (1978), mixed with the Pichia DNA library and allowed to regenerate in a medium deficient in arginine. The transformation resulted in 45 prototrophic yeast colonies from a population of $1 \times 10^7$ total regeneratable spheroplasts. Total yeast DNA was extracted from 7 of the Arg+ colonies and transformed into *E. coli*. Each recovered plasmid was comprised of YEp13 plus insert DNA. To confirm that the Arg+ transforming plasmids contained the Pichia ARG4 gene and not a DNA fragment with suppressor activity, restriction digests of one of the plasmids (pYA33; see FIG. 2) were hybridized to a labelled DNA fragment containing the *S. cerevisiae* ARG4 gene and washed at low stringency. The Pichia DNA portion of the plasmid contained sequences which hybridized to the *S. cerevisiae* ARG4 gene.

Figure 4:
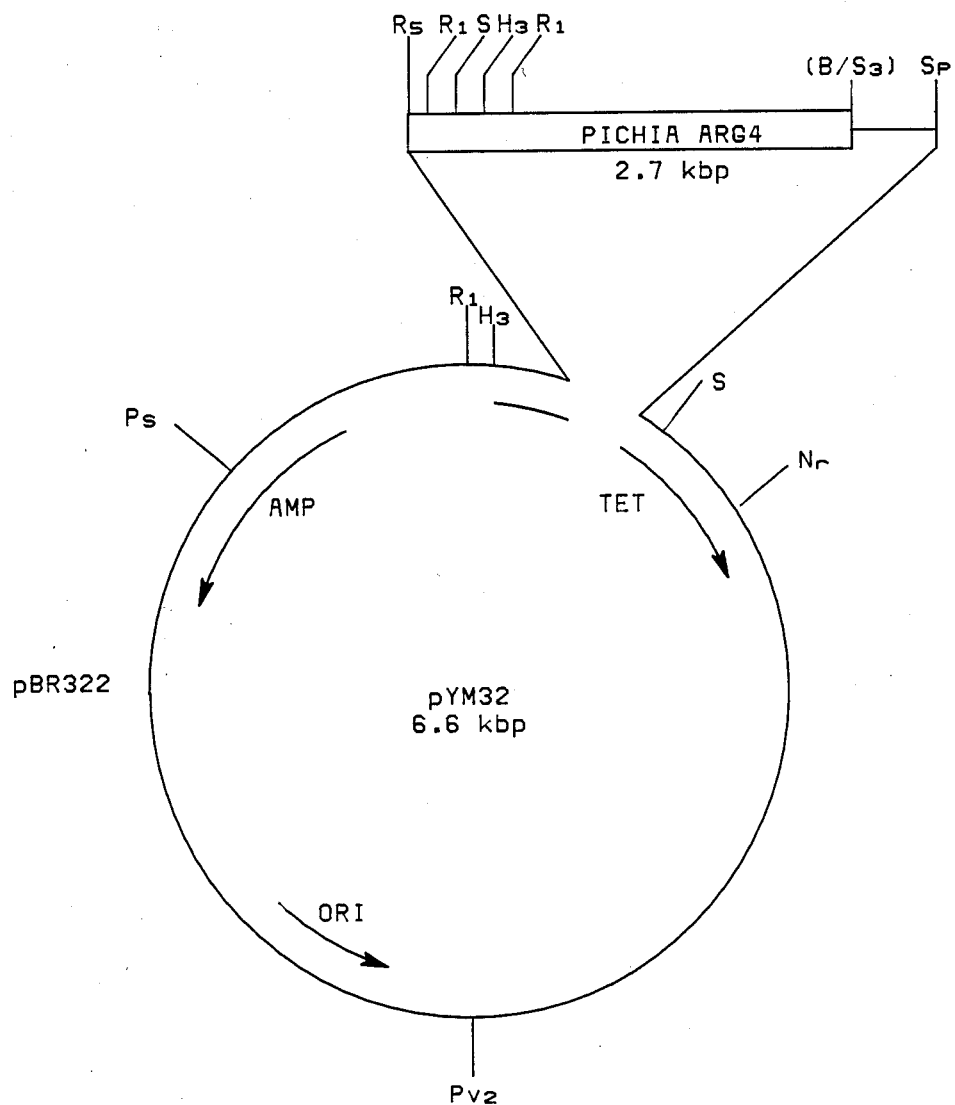
FIG. 4 is a restriction map of plasmid pYM32.

One of the Arg+ transforming plasmids was selected for further characterization. A restriction map of the 8.2 kpb Pichia fragment present in pYA33 is presented in FIG. 3. Plasmid pYA33, carried in the *E. coli* host MC1061, has been deposited with the U.S. Department of Agriculture, Northern Regional Research Center in Peoria, Ill., and assigned the accession number NRRL B-18016. A subfragment of pYA33 capable of transforming the Pichia arg4 mutant NRRL Y-18014 (CS190) at high frequency was a 2.7 kbp EcoRV-SphI fragment (see FIG. 3). For example, pYM30 (see FIG. 5), a plasmid composed of this 2.7 kbp EcoRv-SphI fragment, a Pichia autonomous replication sequence (PARS1) and pBR322, transforms GS190 at high frequency. As another example, pYM32 (see FIG. 4), a plasmid identical to pYM30 only without PARS1, also transform GS190 at high frequency. Since pBR322 sequences are known to not have ARS activity in *P. pastoris*, the 2.7 Kbp fragment containing the Pichia ARG4 gene must have significant ARS activity by the transformation frequency-enhancing definition. This EcoRv-SphI fragment was also capable of transforming the *S. cerevisiae* arg4 mutant S2072A. Smaller subfragments have not been examined, and may well be sufficient to encode the entire functional Pichia ARG4 gene. Thus the ARG4 gene isolated and characterized in accordance with the invention is believed to contain the same gene function which has been identified in *S. cerevisiae* i.e., argininosuccinate lyase.

The examples have been provided merely to illustrate the practice of the invention and should not be read so as to limit the scope of the invention or the appended claims in any way. Reasonable variation and modification, not departing from the essence and spirit of the invention, are contemplated to be within the scope of patent protection desired and sought.

Bibliography

Birnboim and Doly (1979) Nucl. Acids Res. 7, 1513–1523.
Hinnen et al. (1978) Proc. Nat. Acad. Sci., USA 75, 1929–1933.

Rigby et al. (1977) J. Mol. Biol. 113, 237.
Southern (9175) J. Mol. Biol. 98 503–517.
Tschumper and Carbon (1982) J. Mol. Biol. 156, 293–307.

That which is claimed is:

1. A gene isolated from *Pischi pastoris* coding for the production of *Pischi pastoris* argininosuccinate lyase or a subunit thereof which upon expression thereof results in biologically active argininosuccinate lyase.

2. An isolated gene in accordance with claim 1 wherein said gene is characterized by the restriction map in FIG. 3b of the drawings and is obtained by digesting pYA33 with EcoRV and SphI.

3. A DNA fragment isolated from *Pischi pastoris* which comprises a gene coding for argininosuccinate lyase and further comprises flanking regions of *Pichia pastoris* chromosomal DNA as characterized by the restriction map in FIG. 3A of the drawings.

4. *Escherichia coli* NRRL-B-18016; (MC 1061-pYA33).

5. *Pischi pastoris* NRRL Y-18014 (GS 190).

* * * * *